United States Patent
Douglas (12)

(10) Patent No.: US 6,455,324 B1
(45) Date of Patent: *Sep. 24, 2002

(54) EMBOSSED TEST STRIP SYSTEM

(75) Inventor: Joel S. Douglas, Los Altos Hills, CA (US)

(73) Assignee: Amira Medical, Scotts Valley, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/658,000

(22) Filed: Sep. 8, 2000

Related U.S. Application Data

(63) Continuation of application No. 09/215,686, filed on Dec. 18, 1998, now Pat. No. 6,162,639.
(60) Provisional application No. 60/058,307, filed on Dec. 19, 1997.

(51) Int. Cl.[7] ............................................. G01N 33/553
(52) U.S. Cl. ...................... 436/518; 436/541; 436/169; 436/52; 436/805; 436/809; 436/810; 436/823; 436/808; 435/7.1; 435/7.9; 435/7.91; 435/7.92; 435/7.93; 435/7.94; 435/7.95; 435/28; 435/287.1; 435/287.3; 435/288.7
(58) Field of Search ........................... 436/518, 541, 436/169, 52, 805, 809, 808, 810, 823; 435/7.1, 7.9, 7.91–7.95, 28, 805, 810, 287.1, 287.3, 288.7, 970

(56) References Cited

U.S. PATENT DOCUMENTS

| 3,298,789 A | 1/1967 | Mast |
| 4,151,832 A | 5/1979 | Hamer |
| D254,444 S | 3/1980 | Levine |
| 4,360,016 A | 11/1982 | Sarrine |
| 4,503,856 A | 3/1985 | Cornell et al. |

(List continued on next page.)

FOREIGN PATENT DOCUMENTS

| DE | 3708031 | 10/1987 |
| EP | 0 351 891 B1 | 4/1990 |
| EP | 0453283 | 4/1991 |
| EP | 0 759 555 A2 | 2/1997 |
| EP | 0 852 336 A1 | 7/1998 |
| WO | 85/04089 | 10/1984 |
| WO | 95/10223 | 10/1994 |
| WO | 96/32635 | 10/1996 |
| WO | 97/12242 | 4/1997 |
| WO | 97/43962 | 6/1997 |

OTHER PUBLICATIONS

Ash, et al., "A Subcutaneous Capillary Filtrate . . . ," ASAIO Journal, 1993, pp. M699–M705.
Ash, et al., "Subcutaneous Capillary Filtrate . . . " ASAIO Journal, 1992, pp. M416–M420.
Critical Reviews in Biochemical Engineering, vol. 18, issue 1, 1990, pp. 29–54.
Brace, et al., "Reevaluation of the needle . . . ," Amer Jrnal of Phy, v 229, 1975, pp. 603–607.

(List continued on next page.)

*Primary Examiner*—Christopher L. Chin
*Assistant Examiner*—Pensee Do
(74) *Attorney, Agent, or Firm*—Woodard, Emhardt, Naughton, Moriarty & McNett

(57) ABSTRACT

The invention provides a method for measuring the amount of analyte in a sample of biological fluid using a simple low sample volume reagent test strip with a built in metering system. The test strip may comprise a microtitration zone to prevent oversampling and an integrated capillary to prevent problems associated with short sampling and act as means of absorbing the fluid sample. The test strip comprises a wicking layer and a reaction matrix embossed layer in the form of a pillow assembled into a microtitration pocket formed in the strip. The test strip is used in single use applications such as the determination of the concentration of glucose in blood.

10 Claims, 4 Drawing Sheets

U.S. PATENT DOCUMENTS

| | | |
|---|---|---|
| 4,517,978 A | 5/1985 | Levin et al. |
| 4,622,974 A | 11/1986 | Coleman et al. |
| 4,627,445 A | 12/1986 | Garcia et al. |
| 4,637,403 A | 1/1987 | Garcia et al. |
| 4,648,408 A | 3/1987 | Hutcheson et al. |
| 4,653,511 A | 3/1987 | Goch |
| 4,653,513 A | 3/1987 | Dombrowski |
| 4,658,821 A | 4/1987 | Chiodo et al. |
| 4,678,757 A * | 7/1987 | Rapkin et al. ............... 436/169 |
| 4,685,463 A | 8/1987 | Williams |
| 4,787,398 A | 11/1988 | Garcia et al. |
| 4,790,979 A | 12/1988 | Terminiello et al. |
| 4,805,623 A | 2/1989 | Jobsis |
| 4,826,759 A * | 5/1989 | Guire et al. .................... 435/4 |
| 4,850,973 A | 7/1989 | Jordan et al. |
| 4,858,607 A | 8/1989 | Jordan et al. |
| 4,873,993 A | 10/1989 | Meserol et al. |
| 4,883,068 A | 11/1989 | Dechow |
| 4,906,439 A * | 3/1990 | Grenner ....................... 422/56 |
| 4,920,977 A | 5/1990 | Haynes |
| 4,924,879 A | 5/1990 | O'Brien |
| 4,953,552 A | 9/1990 | DeMarzo |
| 4,976,724 A | 12/1990 | Nieton et al. |
| 4,994,068 A | 2/1991 | Hufnagle |
| 4,994,167 A | 2/1991 | Shults et al. |
| 4,994,238 A | 2/1991 | Daffern et al. |
| 4,999,287 A * | 3/1991 | Allen et al. .................... 435/11 |
| 5,002,054 A | 3/1991 | Ash et al. |
| 5,014,718 A | 5/1991 | Mitchen |
| 5,029,583 A | 7/1991 | Meserol et al. |
| 5,035,704 A | 7/1991 | Lambert et al. |
| 5,054,499 A | 10/1991 | Swierczek |
| 5,066,859 A | 11/1991 | Karkar et al. |
| 5,070,886 A | 12/1991 | Mitchen et al. |
| 5,073,484 A * | 12/1991 | Swanson et al. ............ 435/7.92 |
| 5,096,833 A * | 3/1992 | Lau et al. ...................... 435/86 |
| 5,108,889 A | 4/1992 | Smith |
| 5,163,442 A | 11/1992 | Ono |
| 5,164,294 A * | 11/1992 | Skold et al. .................. 435/7.5 |
| 5,165,418 A | 11/1992 | Tankovich |
| 5,178,831 A * | 1/1993 | Sakota et al. ................. 422/56 |
| 5,201,324 A | 4/1993 | Swierczek |
| 5,202,268 A | 4/1993 | Kuhn et al. |
| 5,217,480 A | 6/1993 | Haber et al. |
| 5,223,220 A * | 6/1993 | Fan et al. ...................... 422/58 |
| 5,231,993 A | 8/1993 | Haber et al. |
| 5,277,198 A | 1/1994 | Kanner et al. |
| 5,279,294 A | 1/1994 | Anderson et al. |
| 5,304,468 A | 4/1994 | Phillips et al. |
| 5,318,583 A | 6/1994 | Rabenau et al. |
| 5,318,584 A | 6/1994 | Lange et al. |
| 5,320,607 A | 6/1994 | Ishibashi |
| 5,334,502 A * | 8/1994 | Sangha ....................... 435/7.21 |
| 5,354,692 A * | 10/1994 | Yang et al. .................. 436/514 |
| 5,368,047 A | 11/1994 | Suzuki et al. |
| 5,395,387 A | 3/1995 | Burns |
| 5,402,798 A | 4/1995 | Swierczek et al. |
| 5,418,142 A | 5/1995 | Kiser et al. |
| 5,424,220 A * | 6/1995 | Goerlach-Graw et al. .. 436/568 |
| 5,451,350 A | 9/1995 | Macho et al. |
| 5,515,170 A | 5/1996 | Matzinger et al. |
| 5,569,212 A | 10/1996 | Brown |
| 5,580,794 A | 12/1996 | Allen |
| 5,582,184 A | 12/1996 | Erickson et al. |
| 5,628,309 A | 5/1997 | Brown |
| 5,628,764 A | 5/1997 | Schraga |
| 5,638,828 A | 6/1997 | Lauks et al. |
| 5,668,017 A | 9/1997 | Buchanan et al. |
| 5,682,233 A | 10/1997 | Brinda |
| 5,700,695 A | 12/1997 | Yassinzadeh et al. |
| 5,710,049 A * | 1/1998 | Noppe et al. ................ 436/525 |
| 5,712,172 A * | 1/1998 | Huang et al. ................ 436/518 |
| 5,728,587 A * | 3/1998 | Kang et al. .................. 436/518 |
| 5,730,753 A | 3/1998 | Morita |
| 5,872,713 A | 2/1999 | Douglas et al. |
| 5,948,695 A * | 9/1999 | Douglas et al. ............. 436/518 |
| 6,162,639 A * | 12/2000 | Douglas .................. 435/287.1 |

OTHER PUBLICATIONS

Ginsberg., "An Overview of Minimally . . . ," Clinical Chem, v 38 1992, pp. 1596–1600.

Janle–Swain, et al., "Use of Capillary . . . ," Trans Am Soc Artif Intern Organs, 1987, p 336–40.

Kayashima, et al., "Suction effusion fluid from . . . ," Amer Phys Soc, 1992, pp H1623–1626.

Korthuis, et al., "Interstitium & Lymphatic Techniques," pp 326–327.

Turner, et al., "Diabetes Mellitus: Biosensors for . . . ," Biosensors, 1985, pp 85–115.

International Search Report PCT/US98/27096.

* cited by examiner

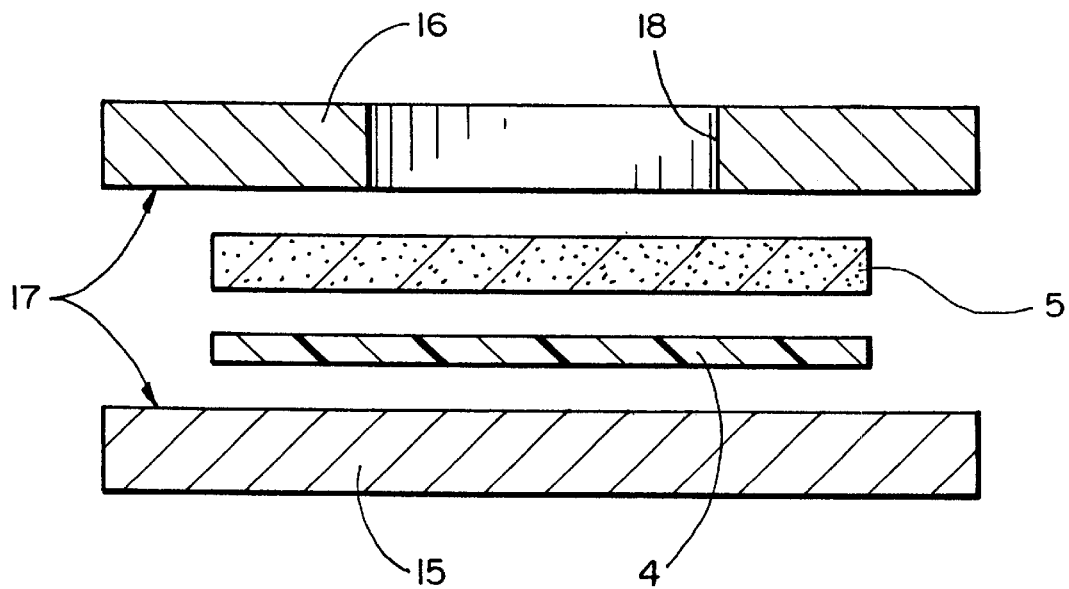
FIG_1
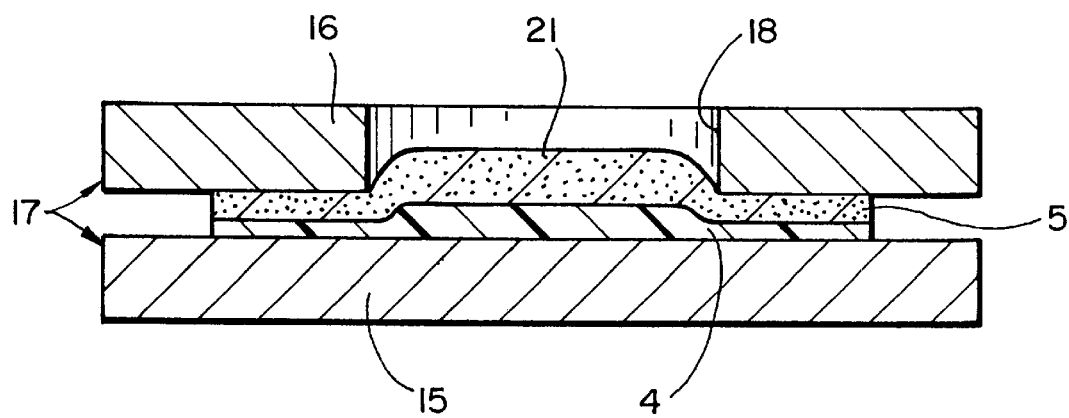
FIG_2

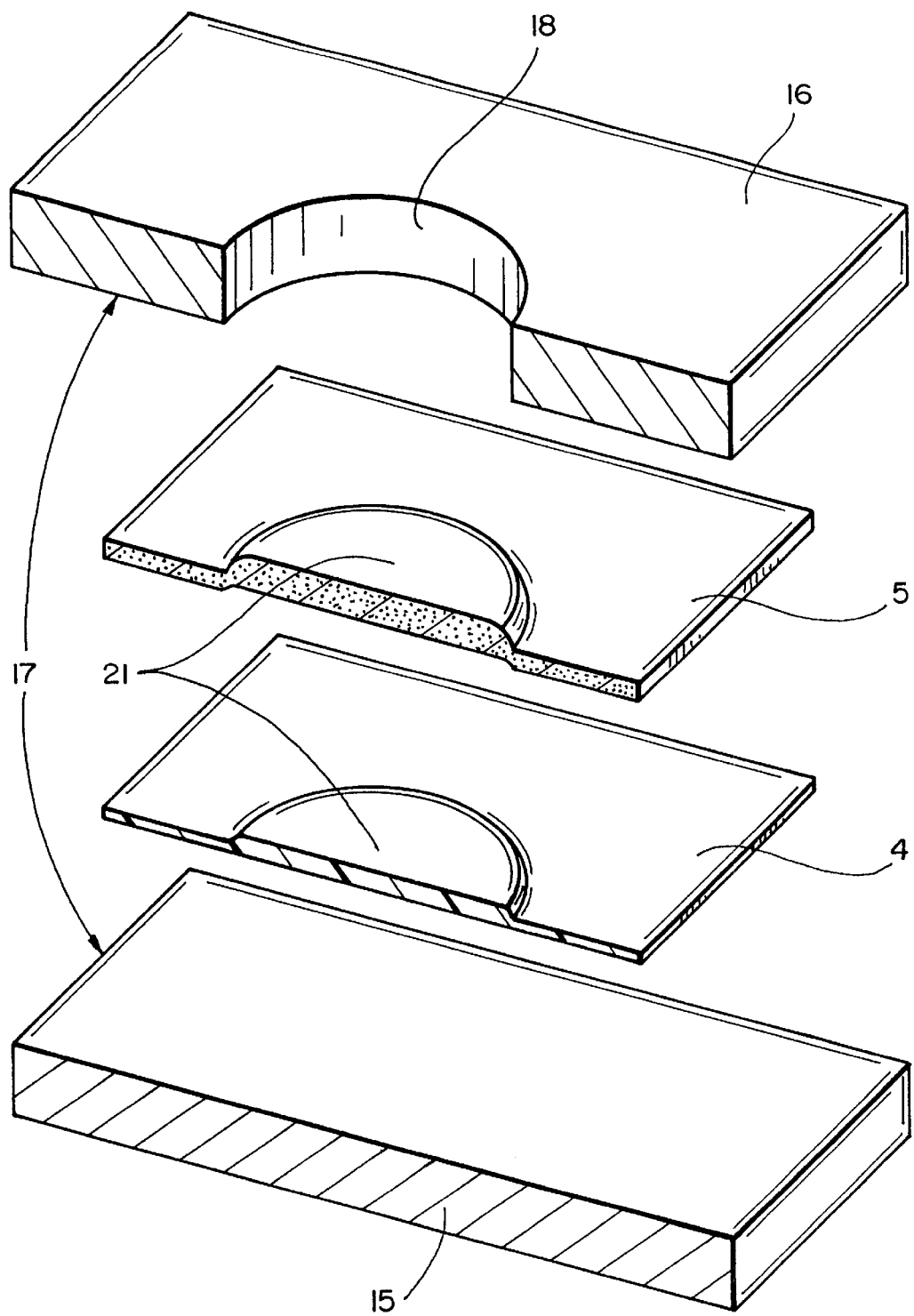
FIG_3

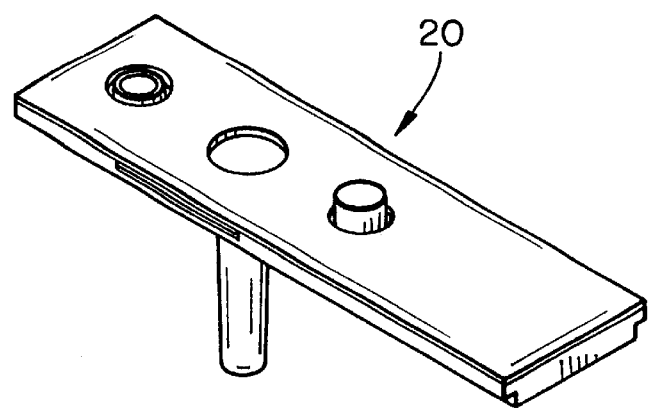
FIG_4A
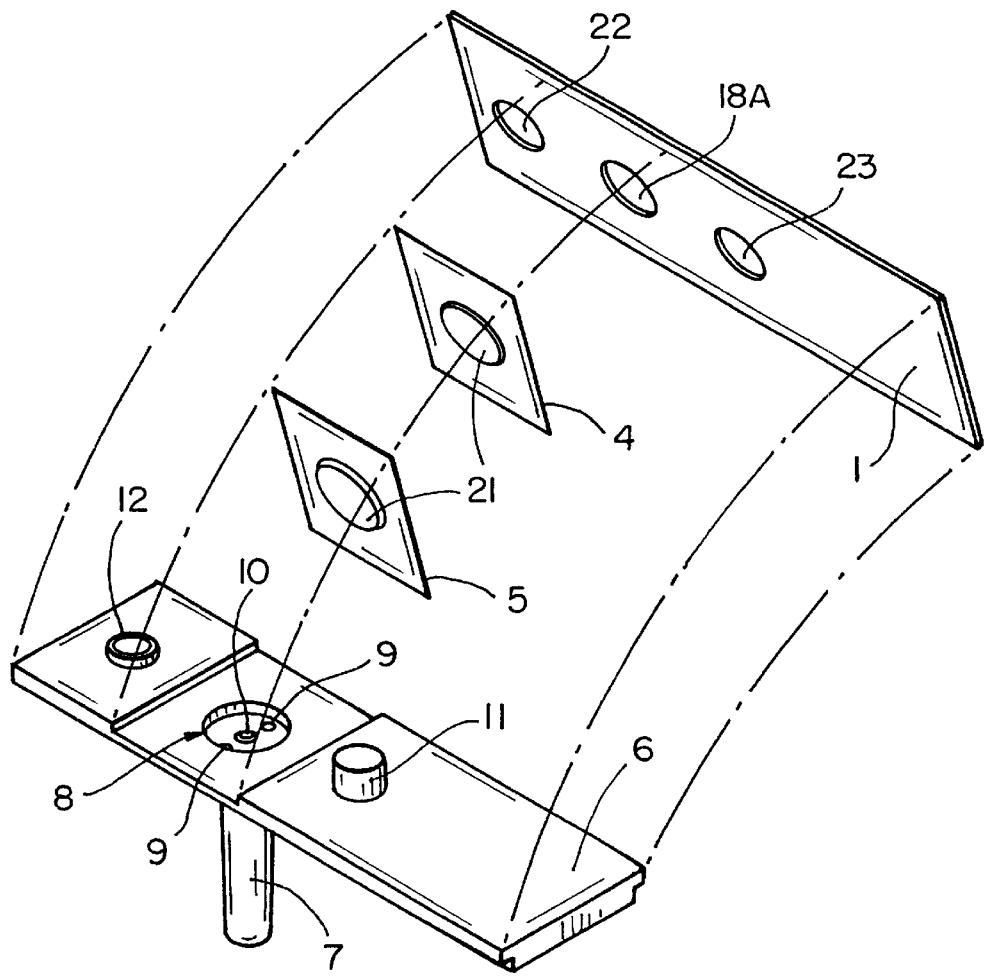
FIG_4B

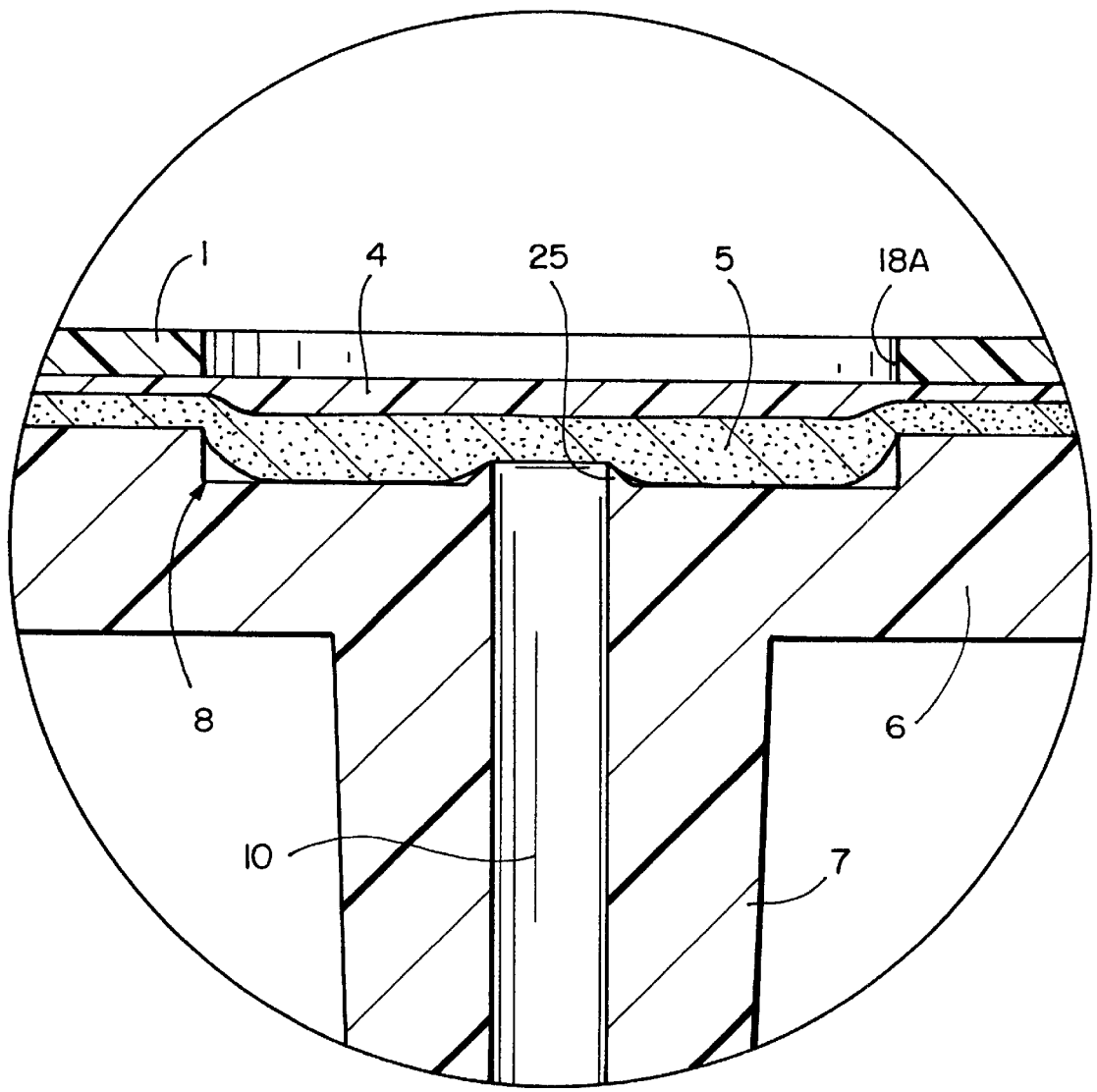
FIG_5

EMBOSSED TEST STRIP SYSTEM

This application is a continuation of Ser. No. 09/215,686 filed Dec. 18, 1998, now U.S. Pat. No. 6,162,639, which claims benefit to Provisional Application 60/058,307 filed Dec. 19, 1997.

FIELD OF THE INVENTION

The present invention relates to a system and method for determining the presence or concentration of analytes or biological agents in a sample of bodily using a specific amount of membrane imbibed with dry reagent. In the most preferred embodiment the meter and a specific quantity of single use reagent bearing test strips are used to measure the concentration of glucose in whole blood.

BACKGROUND OF THE INVENTION

The need for simple methods to determine the chemical and biological constituents in bodily fluids has increased as point of care testing has gained in popularity. The most common application is the self monitoring of blood glucose concentrations by patients with diabetes. Diabetic patients frequently administer insulin or take other therapeutic actions based on the test results. As testing is generally recommended multiple times daily and may occur in any setting, an easy to use low sample volume test is required. The issues associated with sample volume are significant to many diabetic patients, especially elderly patients with compromised circulator systems.

In addition to chronic disease monitoring, there are other applications where simple, low sample size testing at the point of care may be desired. For example, many practitioners believe that certain medications could be administered much more effectively, both from a medical outcomes and from a cost perspective, if the circulating level of such medications could be monitored during the course of treatment. Generally, if the level of an analyte or biological agent is important enough, the patient needs to go to a clinic or laboratory and submit to a venipuncture so a test may be run on an expensive clinical instrument. The ability to monitor the patient either in the doctor's office or at home could lead to improved outcomes. By providing a simple low sample volume test the practitioner is given a means of performing a test utilizing a small sample which in most cases is easier to obtain from the patient by using a simple finger stick.

The National institute of health conducted a large scale study to evaluate the benefit of long term tight control of the blood glucose for the diabetic patient. The study known as the DCCT proved that long term tight control of the blood glucose levels in patients had a direct relationship to the health of the patient. One way for the medical profession to monitor the control of a patient is for the patient to use a blood glucose monitoring system. One of the main obstacles to testing is the sample size needed to perform the test. As patients age and their circulation decreases the ability to extract an adequate sample of body fluid is affected. A test which more efficiently utilizes the body fluid would aid in reducing the problems associated with larger sample size test. Current blood glucose monitoring devices such as the One Touch systems manufactured by LifeScan, Inc. of Milpitas, Calif. require the patient to place between 8 and 12 microliters of blood on the test strip. Many patients apply substantially more blood to the test to minimize the failure of the test due to not enough sample applied to the strip. This unmeasured sample leads to accuracy problems due to more sample than dried chemistry present on the test strip. A system which self meters the amount of sample to a specific amount of carrier consisting of a matrix which holds a relatively constant amount of chemistry and provides a consistent volume for absorbing the sample to promote the test reaction would be a significant advancement to the patient community.

Many diabetics currently use a test method described in U.S. Pat. No. 5,304,468 Phillips et al. This system is comprised of an electronic meter and a disposable reagent strip. The meter reads the color change of the strip which correlates to the concentration of the analyte in the sample applied to the strip. The meter is an expensive and complex instrument which uses multiple light sources or detectors to isolate the reagent color change from the sample color. The user must select the calibration code for the meter to match the calibration code of the test strips. In this way, the meter accommodates a wide range of test strip performance values.

U.S. Pat. No. 4,637,403, Garcia et al., describes an integrated system with provides a method by which the patient lances the finger to get a sample of blood which is then used by the device to read the quantity of analyte in the sample. This system uses a complex reflectance system to read the analyte level in the sample.

U.S. Pat. No. 5,279,294 Anderson et al. describes a hand held shirt pocket device for quantitative measurement of glucose or analytes in biological fluids. The device has sophisticated electronics system and a sampling system integrated into one device to determine the quantity of analyte in a bodily fluid sample.

U.S. Pat. No. 5,515,170 Matzinger et al. describes the difficulties of keeping a strip holder and optics system clean and the need to present the test strip in the proper perspective to the optics.

European Patent Specification 0 351 891 B1 Hill et al. describes an electrochemical system and electrodes which are suitable for the in vitro determination of blood glucose level. The system requires the use of expensive electrodes and a sophisticated reader to determine blood glucose levels.

U.S. Pat. No. 4,994,167 Shults et al. describes a measuring device for determining the presence and amount of a substance in a biological fluid using electrochemical methods. This system requires a complex instrument and method for the patient to determine the quantitative result.

U.S. Pat. No. 5,580,794 Allen et al. describes a single use disposable measuring device for determining the presence and amount of a substance in a biological fluid using reflectance methods. This system utilizes an optics and electronics package which are mated in a single plane.

Single use disposable devices have been designed for the analysis of analytes in bodily fluids. U.S. Pat. No 3,298,789 Mast describes a system in which whole blood is applied to a reagent strip. After a precise, user-timed interval, the blood must be wiped off by the user. An enzyme system reacts with the glucose present in the sample to create a color change which is proportional to the amount of glucose in the sample. The strip may be read visually, by comparing to a printed color intensity scale, or in an electronic instrument.

U.S. Pat. No. 5,418,142 Kiser et al. describes a single use device which does not require blood removal or color matching. The amount of analyte present in the sample is read in a semiquantitative fashion.

U.S. patent application Ser. No. 08/628,489 now U.S. Pat. No. 5,962,215 Douglas et al. describes a series of semiquantitative single use devices which are used to determine the level of an analyte in a biological sample. These devices do not require blood removal or color matching.

U.S. Pat. No. 5,451,350 Macho et al. describes a single use system for the determination of an analyte in a biological sample.

European Patent Application No. EP 0 759 555 A2 Douglas et al. describes a multilayer reagent test strip which measures the concentration of analyte I a liquid sample that is applied to it.

U.S. Pat. No. 4,994,238 Daffern et al. describes a multilayer test device which uses a defined area of absorbent reagent bearing matrix.

Although many improvements have been made, the cost and complexity of measuring analyte levels in biological samples remains a significant issue for patients and for the health care system. The need to deliver a sizable sample of body fluid to the meter and the strips or electrodes in use leads to errors in performance and presents problems for the patient. The availability of a low sample volume which meters the sample to the test matrix reduces the issues with short sampling or over sampling of the test. This is a great advantage to the patient to insure an accurate test. A simplified quantitative test system of this invention for the periodic monitoring of constituents of biological fluids, such as glucose in blood, would make testing more accessible to patients and would improve their well-being.

A system which requires a smaller fluid sample is attractive to many patients. There has been a trend toward smaller sample sizes, but most devices still require about 10 $\mu$L of blood. Many patients have difficulty routinely applying an adequate sample to the strips or electrodes. Inadequate sampling can cause erroneous results or may require that the user discard an expensive test strip and repeat the sample application procedure. A system which would require about 3 $\mu$L, which is a fraction of the volume required for most blood glucose tests and could be more readily obtained by patients, would be advantageous.

An object of the present invention is to provide a method for measuring the amount of analyte in a sample of biological fluid using a simple low sample volume reagent test strip with a built in metering system.

Another object of this invention is to provide reagent test strips that can meter the sample into the reaction matrix.

SUMMARY OF THE INVENTION

The method of this invention involves the use of single use test strips capable of reading small sample sizes and determining the amount of an analyte in the small sample. The low sample size feature of the strip permits the patient to use less invasive systems to acquire a sample than the 21 gauge lancing devices in current use. The device is structured with a capillary to meter a specific quantity of sample to the test matrix there by eliminating a significant source of error associated with short sampling. The capillary is designed so that, when placed in contact with a sample of body fluid, it transfers the sample to the test matrix. If the sample is insufficient to travel the full length of the capillary, then the sample does not reach the test matrix and will not wick into the test matrix, which prevents the patient from short sampling the test strip. They can add additional sample to the capillary to complete the test. Once the sample contacts the test matrix, the sample will wick into the test matrix until the test matrix is filled, then stop. Excess sample remains in the capillary and serves as a signal to the patient that the test matrix has the correct amount of sample for the test. This provides many advantages to the patient including the elimination of wasted strips due to short sampling which results in a substantial cost savings for the patient and reduces the number of inaccurate test from marginal samples.

The capillary design also provides another interesting benefit. As blood travels down through the capillary to the test area, the blood warms the peg, thus regulating the temperature of the strip and the test. This is beneficial in two ways; the first is that each test is performed under somewhat controlled conditions, regardless of whether or not the surrounding temperature is warm or cold. Second, this effect alleviates the problem of fogging over the test area. This is a problem with many blood glucose monitors when testing in cooler ambient conditions.

The formation of a captivated microtitration zone as described in co pending U.S. patent application Ser. No. 08/628,489 now U.S. Pat. No. 5,962,215 Douglas et al. When constructed according to this invention, the microtitration zone can be achieved with a specific volume by following a simple series of steps: (a) applying a specific amount of reagent which is applied such that it does not saturate the matrix and is developed to indicate a specific analyte, (b) drying the reagent so that the active ingredients adhere to the substrate of the matrix, (c) embossing or compressing the matrix to collapse the matrix surrounding the reaction zone so that the void volume of the resulting test matrix microtitration volume is approximately equal to the sample size desired, (d) installing it into a performed pocket which completely surrounds all the circumference of the pillow where the capillary is in communication with the top side/sample side of the pillow, and (e) sealing the system together. The embossed/collapsed areas have had their void volume reduced to approximately zero and the test matrix reaction zone forms a small bibulous pillow which retains its void volume and has the desired total volume. This limits the ability of the reagents imbibed into the embossed matrix to participate in the reaction of the result zone. The test pad can be made from various matrix materials which will hold the test reagent in a dried form including polyethersulphone (Gelman sciences Supor 200D), polysulphone (Memtec filtration asymmetric membrane) and nylon (Pall biodyne). The wicking material which can be selected from various materials including Pall Accuwick and Whatman 41, which provide a high enough capillary action to wick and absorb the sample from the capillary peg and spread it into and fill the reaction matrix microtitration volume.

The applied bodily fluid reacts with the reagents impregnated in the test pad within the test strip and the resulting color change is read by the optics system of the meter adapted to read the strip.

The patient uses the test strip by removing it from the packaging and placing it into a meter designed to utilize the test strip. The patient turns the meter on or it can be automatically started from the test strip insertion. The patient uses the either a sampler from the kit or one procured separately to draw a sample of capillary blood. This sample is applied to the test strip, the meter reads the sample, and the meter displays the result after an appropriate time.

DESCRIPTION OF DRAWINGS

FIG. 1 is an elevation view of one embodiment of a test pad matrix and wicking layer prior to being embossed in a die formed by plates.

FIG. 2 is an elevation view of one embodiment of a test pad matrix and wicking layer during embossing in a die formed by plates.

FIG. 3 is an exploded perspective cut away view of the test pad matrix, wicking layer and upper and lower plates of the embossing die.

FIG. 4A is an assembled view and FIG. 4B is an exploded perspective view of one embodiment of the strip showing assembly of handle, test pad, wicking layer, and capillary.

FIG. 5 is an enlarged cross sectional view of a test strip constructed according to the present invention.

DETAILED DESCRIPTION OF THE INVENTION

The present invention provides improvements over existing technology in use today in several ways. A preferred embodiment of the invention creates a microtitration zone which permits the accurate testing of a small fluid sample and prevents over sampling, while the integrated capillary provides a means to eliminate the problems associated with short sampling which frequently occurs in the current commercial products. The capillary also provides a means of absorbing the fluid sample from a non finger stick location. This permits the use of non traditional lancing systems. The small test pad used in this invention reduces the cost of the matrix employed and the quantity of expensive reagents needed to conduct an accurate assay using an oxidase and peroxidase chemistry. With a smaller test pad, a smaller sample volume is adequate. It should be noted also that an electrode based test system could be used with the basic structure and elements of this invention.

The test strip is comprised of a test pad situated in a test pad holder. This holder provides a means for accurately positioning the test pad with respect to the optics system in the meter and for providing a means for blocking ambient light from affecting the analysis. The test pad is impregnated with the appropriate chemistry to permit a colormetric analysis of the analyte being tested and must therefore provide a stable absorbent substrate. If the system is developed with an electrode base system the function of the test pad holder is position the electrode contacts on the strip with those corresponding to the meter. The test pad can be made from various materials which will hold the test reagent in a dried form, including polyethersulphone (Gelman Sciences Supor 200D), polysulphone (Memtec filtration asymmetric membrane) and nylon (Pall Biodyne). The wicking layer can likewise be selected from various materials, including Pall Accuwick and Whatman 41, which provide a high enough capillary action to absorb the sample and spread it to the reaction matrix.

The test strip of this invention provides a support for the test pad and the capillary peg contacting the test pad. The peg positively seats in the meter in a detent and is locked from rotation by a corresponding key in the test strip which fits into a slot in the meter test strip holder. The test strip holder is positioned to the optics block using pins on the optics block assuring proper alignment of the test strip. It also seals the optics area from ambient light and any excess blood contamination. These features are more fully disclosed in application Ser. No. 08/960,866 filed Oct. 30, 1997, now U.S. Pat. No. 5,872,713 which is incorporated herein by reference.

The signal producing system impregnated in the test pad matrix can be formed from different indicator systems such as 3-methyl-2-benzothiazolinone hydrazone (MBTH) and 8-anilino-1-naphthalenessulfonate(ANS) [U.S. Pat. No. 5,453,360 Yu], MBTH and 3-dimethylaminobenzoic acid (DMAB) [U.S. Pat. No. 5,049,487 Phillips et al.], 3-methyl-2-benzothiazolinone-hydrazone-sulfonate sodium salt (MBTHS) and -Ethyl-N-(3-sulfopropyl)aniline (ALPS) [U.S. Pat. No. 4,396,714 Maeda et al.]. One skilled in the art could devise an alternate indicator system. The oxidase enzyme system contained in the reagent pad produces hydrogen peroxide which is a used to convert the indicator with the assistance of peroxidase which acts as the catalyst.

In the most preferred embodiment the reagents are impregnated into a porous membrane by submerging the dry membrane into a reagent dip. Excess fluid is wiped from the membrane surface and the membrane is gently dried in an oven. At this point, subsequent dipping and drying can be conducted. A preferred embodiment for a two dip process is:

| MBTHS & ALPS Formulation | |
|---|---|
| | Final Concentrations |
| A Dip | |
| In Citrate buffer, pH 7 stock A Dip | 0.1 M |
| EDTA | 0.08% |
| mannitol | 0.19% |
| Gantrez-S95 | 0.53% |
| Klucel 99-EF | 20 uM |
| Crotein-SPA | 7.45% |
| enzyme reagents | |
| Glucose Oxidase | 0.92% |
| Peroxidase | 0.54% |
| B Dip | |
| In 70% Ethanol | |
| MBTHS | 0.66% |
| ALPS | 2.00% |
| SOS | 0.20% |

The color formed after applying the bodily fluid to the reagent test pad is proportional to the amount of analyte in the applied sample. The meter measures the change in reflectance due to the development of the specific color generated by the indicator. This is either used as the input to a function which relates reflectance to analyte level or to a table which correlates reflectance value to analyte level. The function or the table is stored within the meter system for it to produce and display a reading of the analyte level. While most meters in use today employ functions to convert reflectance readings to analyte concentration, this approach requires that the function be stable and well understood. The use of a look up table permits the storage of specific values for reflectance and their corresponding analyte levels. The meter uses this table and interpolates between the table values to give relatively accurate readings. This is achievable in a system such as that described by this invention as the table can quickly be generated for each reagent lot produced. The devices of this invention using a read once calibration chip or being fully disposable can use a lot specific look up table to convert reflectance reading to analyte levels.

FIG. 1 shows an elevation view of the un-embossed layers, wicking layer 5 and test matrix layer 4 between the die 17 formed from top plate 16 containing hole 18 and bottom plate 15.

FIG. 2 shows an elevation view of the embossed or compressed layers, wicking layer 5 and test matrix layer 4 between the die 17 formed from top plate 16 containing hole 18 and bottom plate 15. Hole 18 in die plate 16 forms the microtitration pillow 21 in the wicking layer 5 and in test matrix layer 4. The areas of the layers surrounding pillow 21 are compressed to make them essentially impervious to sample liqud flow, thus forming the microtitration volumetric area around pillow 21.

FIG. 3 shows an exploded perspective view of the embossed or compressed layers, wicking 5 and test matrix 4 as formed between the die 17 formed from top plate 16 and bottom plate 15.

The assembly of a test strip 20 shown in FIG. 4A is accomplished as shown in FIG. 4B. In a preferred embodiment bottom or support member 6 which has the capillary peg 7 and capillary 10 integrally molded therein (e.g., by injection molding) and constructed so that microtitration pocket 8 has breather holes 9 located within the microtitration pocket 8. Or capillary peg 7 can be formed as a separate element and assembled into support member 6 if desired. FIG. 2 shows the formation of the microtitration pillow 21 in matrix 4 and wicking layer 5. The microtitration pillow 21 is formed using die 17 formed from top plate 16 and bottom plate 15. By using a die to form the pillows the spacing of the pillows 21 can be formed in the matrix 4 and wicking 5 so that they align with the microtitration pocket 8. When the top layer 1 is assembled on bottom member 6 with test matrix layer 4 and wicking layer 5 properly positioned as shown between layers 1 and 6. Test matrix pad 4 is formed from a bibulous matrix which has been impregnated with a reagent system comprised of enzymes, indicators and blood separation agents and the wicking matrix pad 5 provides a means of spreading the sample over the test pad 4. Layers or pads 4 and 5 are preferably embossed or compressed prior to assembly with layers 1 and 6. The holes 22 and 23 formed in the top layer 1 and alignment keys 11 and 12 formed in holder 6 provide a means of aligning the test strip assembly including pillow 21 and hole 18A to the microtitration pocket 8. The breather holes 9 provide an escape path for trapped air in the assembly pillow 21 when wicking the sample up the capillary 10 and into pillow 21. FIG. 5 shows an additional preferred feature of the present invention where capillary peg 7 and capillary tube 10 are formed with a protruding collar 25 extending from capillary tube 10 to engage and further compress pillow 21. This feature provides a seal between capillary tube 10 and the surface of wicking layer 5, which better forces the sample flow from capillary tube 10 into the interior of wicking layer 5 to better distribute the sample throughout test matrix layer 4 and completely fill microtitration volume 8 and to better prevent sample from flowing between the surface of wicking layer 5 and the surface of the end of capillary peg 7.

What is claimed is:

1. A low sample volume test strip comprising:
   a top layer;
   a bottom layer;
   a test area disposed between the top and bottom layer, the test area comprising a reaction zone having a predetermined void volume and a precompressed area surrounding the reaction zone, the precompressed area having a void volume of approximately zero; and,
   a capillary constructed to be filled with and deliver a sample to the test area.

2. The test strip of claim 1, wherein the capillary comprises a capillary tube.

3. The test strip of claim 1, wherein the test area comprises a reaction matrix.

4. The test strip of claim 3, wherein the test area further comprises a wicking layer.

5. The test strip of claim 1, wherein the capillary is constructed to be filled with and deliver a sample having a volume of about 3 $\mu$L to the test area.

6. A low sample volume test strip comprising:
   a top layer;
   a bottom layer;
   a test area defining a microtitration zone of a predetermined volume disposed between the top layer and the bottom layer, the test area comprising a reaction zone having a predetermined void volume and a precompressed area surrounding the reaction zone, the precompressed area having a void volume of approximately zero; and,
   a capillary constructed to deliver a sample to the test area.

7. The test strip of claim 6, wherein the predetermined volume is about 3 $\mu$L.

8. The test strip of claim 6, wherein the capillary comprises a capillary tube.

9. The test strip of claim 6, wherein the test area comprises a reaction matrix.

10. The test strip of claim 9, wherein the test area further comprises a wicking layer.

* * * * *